(12) United States Patent
Lesh et al.

(10) Patent No.: US 6,650,923 B1
(45) Date of Patent: Nov. 18, 2003

(54) METHOD FOR ACCESSING THE LEFT ATRIUM OF THE HEART BY LOCATING THE FOSSA OVALIS

(75) Inventors: Michael D. Lesh, Mill Valley, CA (US); Alex K. Khairkahan, Palo Alto, CA (US); Erik J. van der Burg, Sunnyvale, CA (US)

(73) Assignee: ev3 Sunnyvale, Inc., Sunnyvale, CA (US)

( * ) Notice: Subject to any disclaimer, the term of this patent is extended or adjusted under 35 U.S.C. 154(b) by 0 days.

(21) Appl. No.: 09/549,218

(22) Filed: Apr. 13, 2000

(51) Int. Cl.[7] .................................................. A61B 5/00
(52) U.S. Cl. ..................... 600/407; 600/332; 600/341; 600/437; 600/473; 600/476; 600/479; 606/185
(58) Field of Search ..................... 600/473, 475–479, 600/310, 323, 324, 331, 332, 340, 341, 342, 707, 437; 606/185

(56) References Cited

U.S. PATENT DOCUMENTS

| | | |
|---|---|---|
| 3,811,449 A | 5/1974 | Gravlee |
| 4,175,545 A | 11/1979 | Termanini |
| 4,718,417 A | 1/1988 | Kittrell et al. |
| 4,759,348 A | 7/1988 | Cawood |
| 4,827,907 A | 5/1989 | Tashiro |
| 4,960,412 A | 10/1990 | Fink |
| 4,966,150 A | 10/1990 | Etienne et al. |
| 4,998,972 A | 3/1991 | Chin et al. |
| 5,312,341 A | 5/1994 | Turi |
| 5,427,119 A | 6/1995 | Swartz et al. |
| 5,497,774 A | 3/1996 | Swartz et al. |
| 5,499,975 A | 3/1996 | Cope et al. |
| 5,558,093 A | 9/1996 | Pomeranz |
| 5,558,652 A | 9/1996 | Henke |
| 5,722,400 A | 3/1998 | Ockuly et al. |
| 5,724,975 A | 3/1998 | Negus et al. |
| 5,725,512 A | 3/1998 | Swartz et al. |
| 5,807,261 A * | 9/1998 | Benaron et al. ............ 600/473 |
| 5,814,028 A | 9/1998 | Swartz et al. |
| 5,814,029 A | 9/1998 | Hassett |
| 5,820,591 A | 10/1998 | Thompson et al. |
| 5,833,673 A | 11/1998 | Ockuly et al. |
| 5,840,027 A | 11/1998 | Swartz et al. |
| 5,848,969 A | 12/1998 | Panescu et al. |
| 5,879,296 A | 3/1999 | Ockuly et al. |
| 6,004,280 A | 12/1999 | Buck et al. |
| 6,066,126 A | 5/2000 | Li et al. |
| 6,090,084 A | 7/2000 | Hassett et al. |
| 6,203,531 B1 | 3/2001 | Ockuly et al. |
| 6,285,898 B1 * | 9/2001 | Ben-Haim ................. 600/407 |

FOREIGN PATENT DOCUMENTS

| | | |
|---|---|---|
| FR | 2 481 917 | 11/1981 |
| SU | 1297782 A1 | 3/1987 |

OTHER PUBLICATIONS

*Transseptal Left Heart Catheterization: Usefulness of the Intracavitary Electrocardiogram in the Fossa Ovalis*, Hector Bidoggia, MD, Juan P. Maciel, MD, and Jose A. Alvarez, MD., Catheterization Diagnosis 24:221–225 (1991).

* cited by examiner

Primary Examiner—Ruth S. Smith
(74) Attorney, Agent, or Firm—Knobbe, Martens, Olson & Bear, LLP

(57) ABSTRACT

Disclosed is an access catheter for identifying and providing access through a tissue structure such as the fossa ovalis on the intraatrial septum. The access catheter comprises an elongate flexible tubular body having a proximal and a distal end, and a retractable piercing structure such as a needle carried by the distal end. A detector such as a red, green, and blue light detector is associated with the access catheter, such that placement of the distal end of the catheter against the fossa ovalis can be detected. The piercing structure is thereafter advanceable to provide access to the left atrium through the fossa ovalis.

37 Claims, 6 Drawing Sheets

METHOD FOR ACCESSING THE LEFT ATRIUM OF THE HEART BY LOCATING THE FOSSA OVALIS

BACKGROUND OF THE INVENTION

The present invention relates to transeptal access systems for accessing the left atrium from the right atrium by crossing the fossa ovalis. In particular, the present invention relates to devices and methods for locating the fossa ovalis.

The typical human heart includes a right ventricle, a right atrium, left ventricle and left atrium. The right atrium is in fluid communication with the superior vena cava and the inferior vena cava. The tricuspid valve separates the right atrium from the right ventricle. On the inner wall of the right atrium where it is separated from the left atrium is a thin walled, recessed portion, the fossa ovalis. In the heart of a fetus, the fossa ovalis is open (patent foramen), permitting fetal blood to flow between the right and left atria, bypassing the fetal lungs in favor of the placental blood flow. In most individuals, this opening closes after birth. In as many as about 5 percent of adults an opening (the patent foramen) still remains in place of the fossa ovalis between the right and left atria.

A wide variety of diagnostic and therapeutic procedures have been developed in which a catheter is transluminally advanced into various chambers and across valves of the heart. The most difficult chamber of the heart to access with a catheter is the left atrium. Access to the left atrium through the pulmonary artery is not possible. Approaches from the left ventricle are difficult, may cause arrhythmias and may present difficulty in obtaining stable catheter positioning. Accordingly, the presently preferred method of accessing the left atrium is through a transeptal approach, achieved by catheterization of the right atrium with subsequent penetration of the interatrial septum. The reduced wall thickness and location of the fossa ovalis makes it a useful access point for a transeptal access puncture.

A variety of risks are attendant to transeptal catheterization, in addition to the risks associated with normal heart catheterization. The primary additional risk is that associated with inaccurate identification and localization of the atrial septum and the fossa ovalis in particular. Improper placement of the catheter tip prior to the transeptal puncture presents the risk of puncture of tissue other than the interatrial septum, such as the aorta and the posterior wall of the right or left atrium. For this reason, catheterization is accompanied by fluoroscopy or other visualizing techniques to assist in properly locating the catheter tip in relation to the septum.

The objectives of left atrial access can be either diagnostic or therapeutic. One diagnostic use is pressure measurement in the left atrium. In the setting of an obstructed mitral valve (mitral stenosis), left atrial access allows a determination of the pressure difference between the left atrium and left ventricle. Left atrial access also allows entry into the left ventricle through the mitral valve. This is desirable when an artificial aortic valve is in place. The advent of aortic valve replacement with mechanical artificial valves, and the increase in the aged population and growing longevity of that population subsequent to aortic valve replacement, brings a greater need to evaluate the late stage functionality of such artificial valves.

Diagnostic measurement of the left ventricular pressures are, therefore, desirable to allow evaluation of mechanical artificial aortic valves post-replacement. It may be unsafe to cross these mechanical artificial valves retrograde from the aorta; therefore, access to the left ventricle by the antegrade route using a transeptal puncture is the preferred approach. Once a catheter has been placed in the left atrium using the transeptal approach, access to the left ventricle can be gained by advancing catheters across the mitral valve.

Many diagnostic indications exist for left atrial pressure measurements in addition to evaluating the functionality of artificial mitral valves. Other diagnostic indications for accessing the left ventricle via the antegrade transeptal approach include aortic stenosis, when a cardiologist is unable to pass a catheter retrograde into the left ventricle, and some disease states where the antegrade approach is considered preferable, such as subaortic obstruction.

Presently, the therapeutic objectives of left atrial access are primarily two-fold. The first is mitral valvuloplasty which represents an alternative to surgical procedures to relieve obstruction of the mitral valve. The second therapeutic objective is for electrophysiological intervention in the left atrium. Catheter ablation involves the placement of energy (typically RF) through a catheter, into various locations of the heart to eradicate inappropriate electrical pathways affecting the heart function. When these locations are in the left atrium, the catheter through which the radio frequency generator is placed typically is itself placed with transeptal catheterization. More recently, therapeutic treatment of the left atrial appendage to reduce the risk of embolic stroke has also been proposed.

Despite clinical acceptance of a wide variety of procedures which require access to the left atrium, significant room for improvement remains in the actual access technique. For example, the step of locating an appropriate site on the septum such as the fossa ovalis is highly technique dependant and can be inaccurate. This increases procedure time, and creates a risk that the needle will pierce the heart wall in an unnecessary and potentially undesirable location. Thus, there remains a need for a device and method for quickly and accurately locating and piercing the fossa ovalis to permit rapid and accurate transeptal access.

SUMMARY OF THE INVENTION

In accordance with one aspect of the present invention, there is provided a method of locating the fossa ovalis. The method comprises the steps of positioning the distal tip of a catheter in the heart, and propagating a signal from the catheter. A return signal is received by the catheter, and the tip of the catheter is moved to a position in which the return signal is indicative of the fossa ovalis.

In one embodiment, the propagating a signal step comprises propagating an ultrasound signal. Alternatively, the propagating a signal step comprises propagating an electromagnetic signal such as a signal in the UV-visible or IR range. Preferably, the electromagnetic signal comprises multiple wavelengths, including at least one of red, green and blue light.

In accordance with another aspect of the present invention, there is provided a trans septal access system. The system comprises a sheath, a dilator, a needle, and a signal transmitting surface and a signal receiving surface on at least one of the sheath, dilator and a needle, for transmitting a signal and receiving a return signal.

In one embodiment, the signal transmitting surface and the signal receiving surface comprise the same surface. The signal transmitting surface and/or the signal receiving surface may be the distal end of a waveguide. Alternatively, the signal transmitting surface and/or signal receiving surface may be a transducer. Preferably, the system further comprises a source of light, such as red, green and blue light, in communication with the signal transmitting surface. A detector capable of evaluating the frequency and intensity of the return signal is provided in communication with the signal receiving surface.

In accordance with a further aspect of the present invention, there is provided a method of locating the fossa ovalis. The method comprises the steps of bringing a catheter into contact with the surface of the septum between the right and left atria, and moving the catheter along the septum. Color absorption either within or beyond the septum is monitored for a change which is indicative of the location of the fossa ovalis. Preferably, the monitoring step comprises detecting reflected light. Thus, the method preferably comprises the step of transmitting light distally through the catheter to the septum, and receiving reflected light proximally through the catheter to a detector.

Further features and advantages of the present invention will become apparent to those of ordinary skill in the art in view of the detailed description of preferred embodiment which follows, when considered together with the attached drawings and claims.

DETAILED DESCRIPTION OF THE PREFERRED EMBODIMENT

Figure 1:
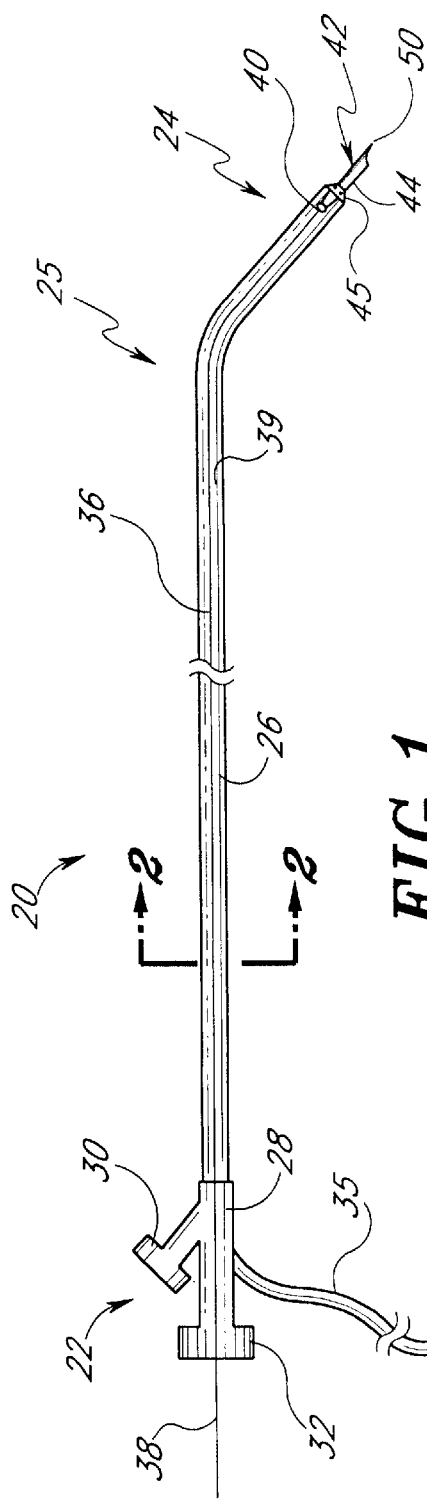
FIG. 1 is a side elevational schematic view of a transeptal access system in accordance with the present invention.

Referring to FIG. 1, there is disclosed a dilator 20 in accordance with the present invention. Dilator 20 has a proximal end 22, a distal end 24 and an elongate flexible tubular body 26. The overall length of the dilator 20 depends upon the percutaneous access point and the desired application. For example, lengths in the area of from about 80 cm to about 100 cm are typical for use in percutaneous transluminal access at the femoral vein for locating and puncturing a site on the atrial septum in the heart.

Tubular body 26 may be manufactured in accordance with any of a variety of known techniques, for manufacturing catheters adapted to reach the coronary arteries or chambers of the heart. For example, tubular body 26 may be manufactured as an extrusion of appropriate biocompatible polymeric materials such as high density polyethylene, polytetrafluoroethylene, nylons, and a variety of others which are known in the art. Blended materials may also be used, such as HDPE (e.g., HDPE/LDPE ratios such as 50%:50%, 60%:40% and others) with from about 5% to about 25%, and, in one embodiment, about 20% $BaSO_4$ for lubricity and radiopacity. Alternatively, at least a portion or all of the length of tubular body 26 may comprise a spring coil, solid walled hypodermic needle tubing (eg, stainless steel, NiTi alloys) or braided reinforced wall as is understood in the catheter and guidewire arts.

For most applications, the tubular body 26 is provided with an approximately circular cross sectional configuration having an outside diameter within the range of from about 0.020" to about 0.200". In accordance with one embodiment of the invention, the tubular body 26 has an outside diameter of about 0.160" throughout its length. Other lengths and diameters may be readily utilized, depending upon the desired profile and performance characteristics.

The proximal end 22 is provided with a manifold 28, having one or more access ports as in known in the art. In the illustrated embodiment, manifold 28 is provided with a core wire port 32 which may also or alternatively function as a guidewire port in an over the wire embodiment. An injection port 30 may also be provided, for injecting a contrast media, such as to confirm that the distal end 24 has traversed the intraatrial septum. Additional access ports may be provided as needed, depending upon the functional capabilities of the catheter. Manifold 28 may be injection molded from any of a variety of medical grade plastics or formed in accordance with other techniques known in the art.

The proximal end 22, either at the manifold 28 or distally of the manifold 28 is also provided with a communication line 34 such as a fiber optic bundle 35 in accordance with one aspect of the present invention. In one embodiment of the invention, fiber optic bundle or signal transmitting line 35 communicates with a signal (e.g. sound, light, ultrasonic or other vibration, etc.) generator and detector 37. In this embodiment of the invention, the detector 37 enables the catheter to distinguish among solid tissue or a thick membrane, a thin membrane such as at the fossa ovalis, and right atrial or left atrial chamber blood beyond the distal end 24 of dilator 20 as will be discussed.

The flexible body 26 is provided with a preset bend 25, for assisting in biasing the distal end 24 against the intraatrial septum as is understood in the art. Bend 25 preferably has a radius within the range of from about 0.5 cm to about 5 cm and, in one embodiment, about 2.5 cm. Bend 25 is centered on a point which is within the range of from about 1 cm to about 10 cm proximally from distal end 24. In one embodiment, the bend 25 is centered at approximately 6 cm proximally from distal end 24. The bend 25 is defined by a proximal transition where it meets the substantially linear proximal portion of the dilator 20, and a distal transition where it meets the substantially linear distal portion of the dilator 20. The angular deflection of the bend 25 is generally within the range of from about 30° to about 80° and, in one embodiment, is about 50°.

Bend 25 may be provided in accordance with any of a variety of techniques. For example, in an embodiment of tubular body 26 which includes a hypotube or other metal tubing, the tubular body 26 may be bent such as around a forming mandrel in excess of the elastic limit of the hypotube. Alternatively, an injection molded catheter body may be heat set in a predetermined bend, such as with removable flexible mandrels extending through any interior lumen to maintain patency of the lumen around the bend. Other techniques will be known to those of skill in the art. Alternatively, the bend 25 may be formed during or after placement of the catheter in the heart. This may be accomplished by providing the catheter with any of a variety of steering mechanisms, which allow a distal portion of the catheter to be inclined away from the axis of the normal bias of the catheter. For example, one or more axially moveable pull wires may extend throughout the length of the catheter. Proximal traction on a pull wire which is secured at the distal end of the catheter will cause a lateral defection of the catheter.

Figure 3:
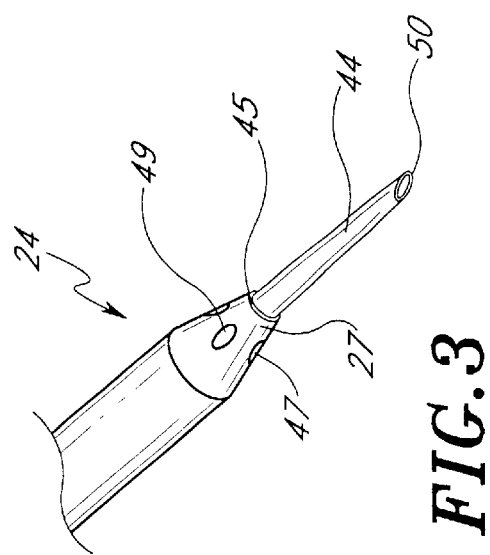
FIG. 3 is an enlarged perspective view of the distal end of the transeptal access system of FIG. 1.

Referring to the enlarged schematic illustration of FIG. 3, distal end 24 is provided with at least one signal transmitting surface 47 and at least one signal receiving surface 49. Transmitting surface 47 is adapted to transmit a signal from the distal end 24 of dilator 20 and generally in the distal direction with respect to the dilator. Receiving surface 49 is adapted for receiving a reflected return signal traveling in a generally proximal direction with respect to the distal end 24 of dilator 20. In one embodiment, the transmitting surface 47 comprises the distal end of a fiber optic or fiber optic bundle, or a transparent window positioned at the distal end of a fiber optic or fiber optic bundle. Similarly, the receiving surface 49 comprises a distal end of a receiving fiber optic or a transparent window positioned distally of the receiving fiber optic. In the illustrated embodiment, two transmitting surfaces 47 and two receiving surfaces 49 are provided each communicating with the spectrometer 37 via a unique communication line 34.

Transmission and reception of, for example, visible light, can alternatively be accomplished though a single transparent window, and embodiments in which the transmission and reception signals are propagated through the same fiber optic or through closely adjacent fiber optics are also contemplated. Propagation of transmission and reception signals through the same fiber optic can be accomplished such as by the provision of a coupler at the proximal end to split the transmission and reception signals for processing at detector 37 as will be understood in, among others, the blood oximetry detector arts. Alternatively, one or more separate transmit surfaces 47 and receiving surfaces 49 may be provided, and anywhere within the range of from about 1 to about 12 of each transmit surface 47 and receiving surface 49 may be provided as desired.

Signal transmitting bundle 35 thus provides communication between the transmit surface 47 and receiving surface 49, and a detector 37 such as a spectrometer which remains outside of the patient. The construction and use of spectrometers such as to measure RGB and other UV, visible and IR wavelengths is well understood in the pulse oximetry art, among others, and will not be disclosed in detail herein. In general, transmitter/detector 37 is able to transmit multiple wavelengths of light, which propagate beyond the transmit surface 47 and into a target beyond the distal end 24 of the dilator 20. Some of the transmitted light is absorbed in the target, while other transmitted light is reflected back and received at receiving surface 49. The reflected light is thereafter propagated to the light detector 37 for processing. The present inventors have determined that the light detector 37 in combination with the dilator of the present invention can identify when the distal end 24 of the dilator 20 is positioned against the fossa ovalis of the intraatrial septum, as opposed to other portions of the septum or muscle wall, due to the unique characteristics of light observed at the fossa ovalis.

Depending upon the characteristics of the transmitted light, reflected light at the fossa ovalis will exhibit unique characteristics imparted by (1) light reflected at the surface of or within the fossa ovalis, (2) light reflected through the fossa ovalis by blood in the left atrium, or (3) a combination of the foregoing. The ability of an optical detector to locate the fossa based upon light propagated through the fossa is based upon several circumstances. The blood in the right atrium is relatively poorly oxygenated, and therefore more blue than red. The left atrium contains well oxygenated blood which tends to be relatively red. The fossa is thin enough to allow light to be transmitted across the fossa and into and from the left atrium while the fossa locator is still on the right atrial side. All other areas of the septum are generally thick enough that they will not allow significant light transmission between the right atrium and the left atrium. Thus, in an embodiment of the invention which utilizes light transmission through the fossa, the location of relatively red blood indicates transmission into the left atrium which will generally only happen at the fossa.

Alternatively, the septum contains oxygenated blood and therefore has a certain level of red transmission. The fossa, however, is a thin translucent membrane which is almost yellow. Non-oxygenated blood within the right atrium is relatively blue, while oxygenated blood within the left atrium is red. Location of the fossa may thus alternatively be accomplished by identifying the presence of a translucent, near yellow membrane. The use of multiple wavelengths, transmission, and detectors will allow assessment of both the near yellow color of the fossa, as well as the red color identified through the fossa as will be apparent to those of skill in the art in view of the disclosure herein.

The method of the present invention may additionally be accomplished by providing a light source within the left atrium. The left atrium light source may be provided on any of a variety of left atrium access catheters, as will be apparent to those of skill in the art. Light generated in the left atrium, will be detectable in the right atrium either exclusively at the fossa, or with a greatest intensity appearing at the fossa. Thus, the left atrium dilator 20 need only be provided with light detector optics and electronics, to identify the fossa based upon the characteristics of light received from the right atrium light source.

The dilator 20 is additionally provided with a tissue piercing structure 42 such as a needle 44. Needle 44 preferably comprises a tubular structure such as a stainless steel hypotube having a sharpened distal end 50. The sharpened distal end 50 of needle 44 is axially moveable advanceable through an aperture 45 in the distal end 24 of the tubular body 26.

In one embodiment of the invention, the needle 44 has an axial length of from about 1 cm to about 5 cm, an inside diameter of about 0.022 inches and an outside diameter of about 0.032 inches. Any of a variety of other dimensions for needle 44 may also be used depending upon the desired performance and overall catheter dimensions. Needle 44 is connected to the distal end 40 of a control element such as core wire 36 which axially moveably extends throughout the length of tubular body 26. The proximal end 38 of the core wire 36 in the illustrated embodiment extends proximally from the core wire port 32. The needle 44 is preferably axially moveable between a first position in which the tip 50 is contained within the distal end 24 of the tubular body 26 and a distal position in which the distal tip 50 of the needle 44 is exposed beyond the distal end of the body 26 such as for piercing the fossa ovalis. Distal advancement of the proximal end 38 of core wire 36 will advance the needle 44 from the first position to the second position as will be appreciated in view of the disclosure herein. Alternatively, the needle 44 and core wire 36 may be removed entirely from the dilator 20 except when desired to pierce the septum.

The proximal end 38 of the core wire may be exposed beyond the proximal end of core wire port 32 as in the illustrated embodiment, such that the physician can grasp the core wire 36 and advance it distally with optimum tactile feedback. Alternatively, the proximal end 38 of core wire 36 may be connected to any of a wide variety of controls such as a slider switch, rotatable knob or other control attached to or adjacent the manifold 28. Manipulation of the control can controllably reciprocally move the needle 44 between the first and second position.

In an alternate embodiment, disclosed in FIGS. 6–10, the needle 44 removably extends throughout the entire length of the dilator 20. For this embodiment, needle 44 may have an axial length of from about 100 cm to about 120 cm or longer, and, in one embodiment, about 110 cm.

In the illustrated embodiment, radiopaque dye can be injected through the central lumen 39, and through the hollow needle 44 (if present) for assessing the position of the distal end 24 of the dilator 20. Alternatively, blood may be withdrawn and analyzed for $O_2$ content by well known methods. Left atrial blood will have an $O_2$ saturation of greater than 90%, whereas right atrial blood has an $O_2$ saturation of less than 80%. A separate injection lumen (not illustrated) can be readily provided if desired for a particular application. In addition, the needle 44 may be removable from the dilator 20. In this construction, the dilator 20 retains its greatest flexibility such as for advancement to the intraatrial access site. Once the distal end 24 of the dilator 20 is positioned within the left atrium, the piercing structure 42 such as needle 44 can be loaded into the proximal end 22 of the dilator 20 and advance distally throughout the length of the dilator 20 and out a distal aperture 45. Once the piercing structure 42 has pierced the fossa ovalis or other structure, and the distal end 24 of the dilator 20 is advanced through the opening formed by the piercing structure, the piercing structure 42 may be proximally retracted and removed from the dilator, thereby leaving the central lumen fully available for subsequent therapeutic or diagnostic devices or materials.

Preferably, the distal end 24 of dilator 20 is provided with a tapered frustro conical surface 27. This allows the tubular body 26 to function as a dilator, thereby permitting the tapered surface 25 to enlarge the opening formed by needle 44 while minimizing "tenting" of the fossa ovalis during the transeptal access procedure.

In accordance with the method of the present invention, the right atrium may be initially accessed with a transeptal access system through either the inferior or superior vena cava, which initially requires cannulation with an introducer sheath such as through the well known "Seldinger" technique. The transeptal access system of the present invention includes a transeptal sheath, a piercing dilator catheter 20 as discussed above, and an appropriately sized guidewire.

In present practice, the preferred access point is along the right femoral vein, although access from the left femoral vein is also possible. Access may also be achieved through a puncture in any of a variety of other veins of suitable internal diameter and the present invention is not limited in this regard.

A conventional spring tipped guide wire is thereafter advanced through the needle into the vein and the needle is subsequently removed. The dilator 20 of the present invention is positioned within a sheath such as a 14 French introducer sheath. Subsequently, the sheath and inner dilator 20, in combination with the guide wire, are advanced through the femoral vein to the right atrium.

Figure 4:
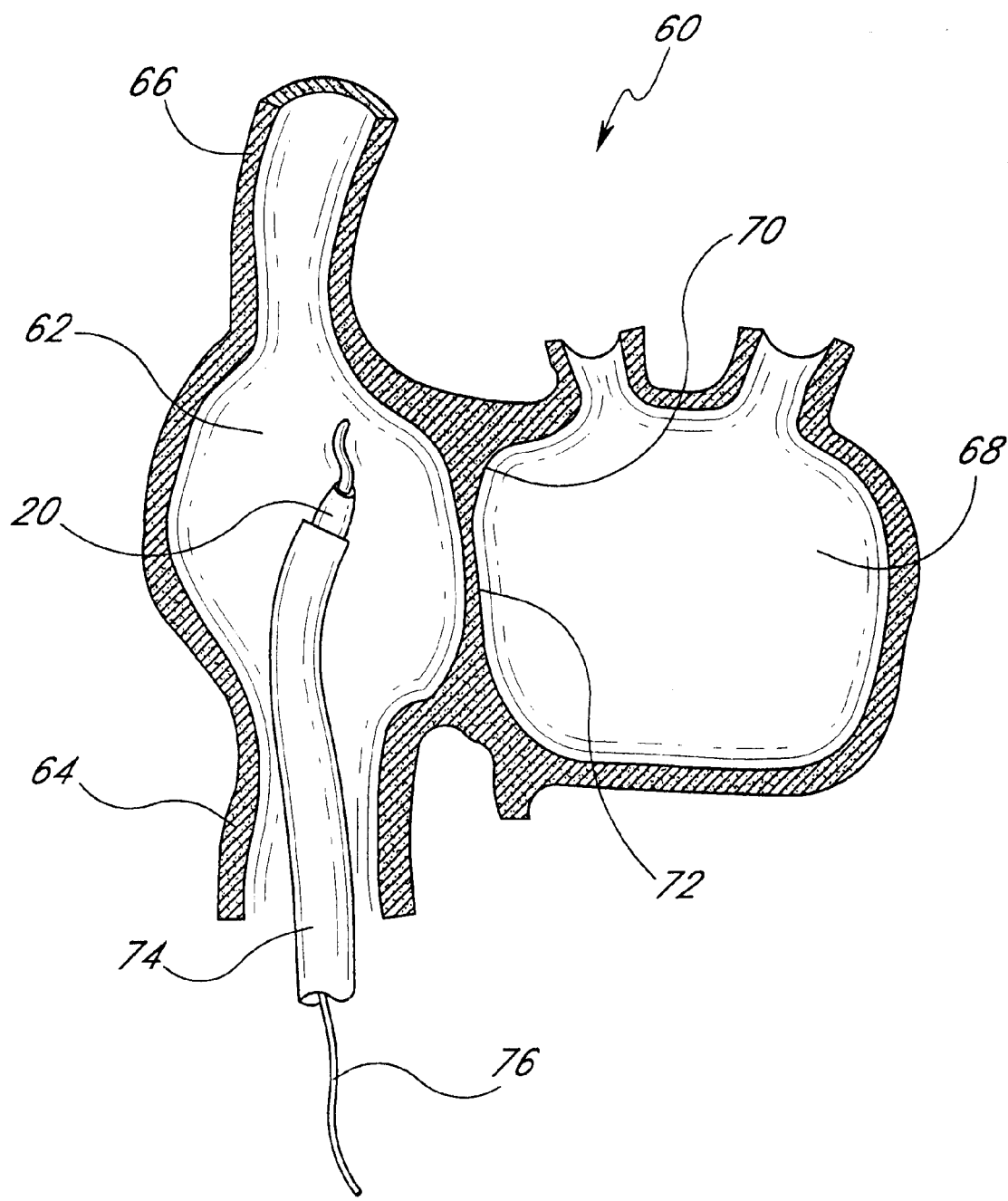
FIG. 4 is a schematic cross-sectional view of a portion of the heart, showing a trans septal access catheter of the present invention within the right atrium.

Referring to FIG. 4, there is illustrated a schematic cross-section of a portion of the heart 60. The right atrium 62 is communication with the inferior vena cava 64 and the superior vena cava 66. The right atrium 62 is separated from the left atrium 68 by the intraatrial septum 70. The fossa ovalis 72 is located on the intraatrial septum 70. As seen in FIG. 4, the sheath 74 having the dilator 20 therein and a guidewire 76 have been positioned within the right atrium 62.

Figure 5:
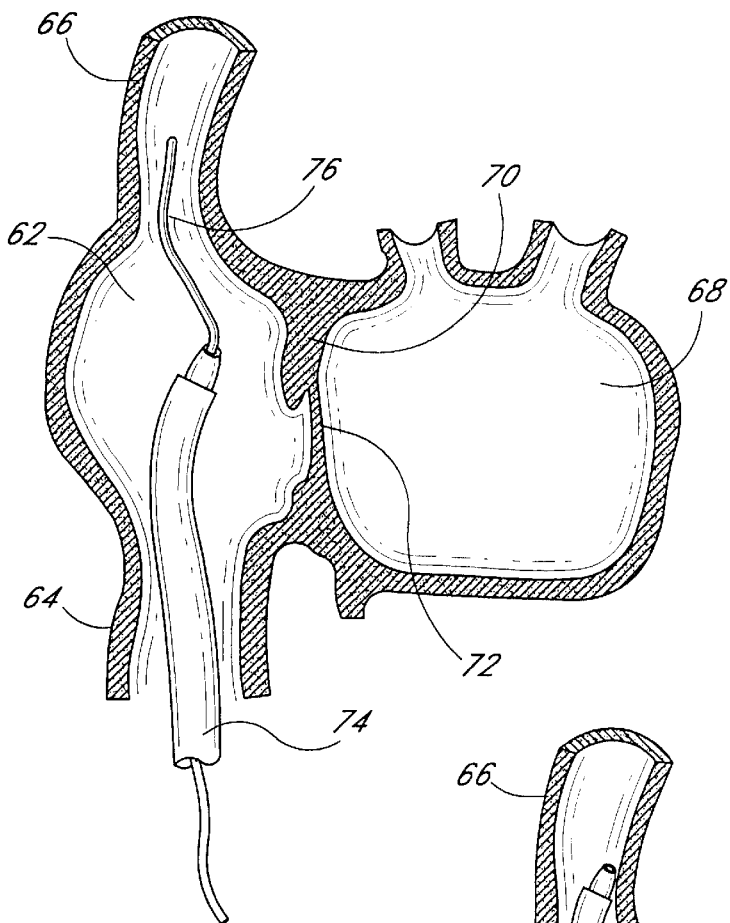
FIG. 5 is a cross-sectional view as in FIG. 4, with the guidewire positioned in the superior vena cava.
Figure 6:
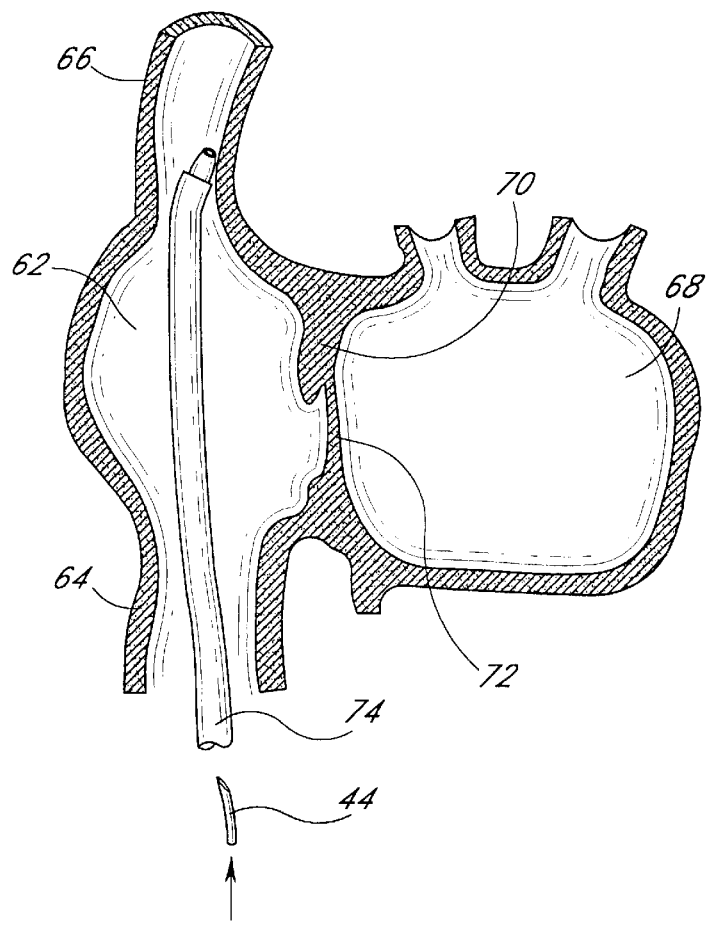
FIG. 6 is a cross-sectional view as in FIG. 4, with the trans septal access catheter positioned against the wall of the superior vena cava.
Figure 7:
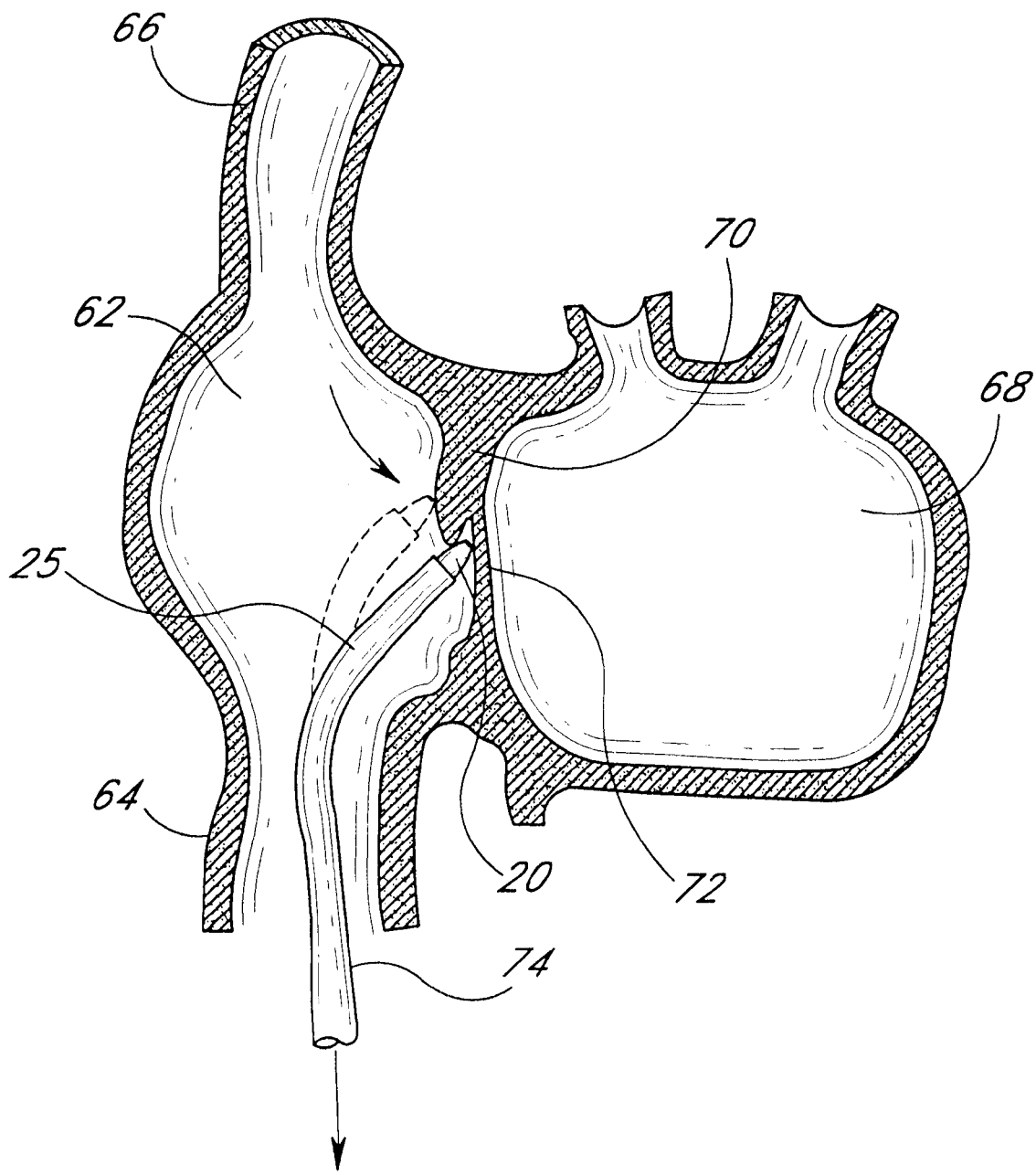
FIG. 7 is a cross-sectional view as in FIG. 4, with the access catheter positioned against the fossa ovalis.
Figure 8:
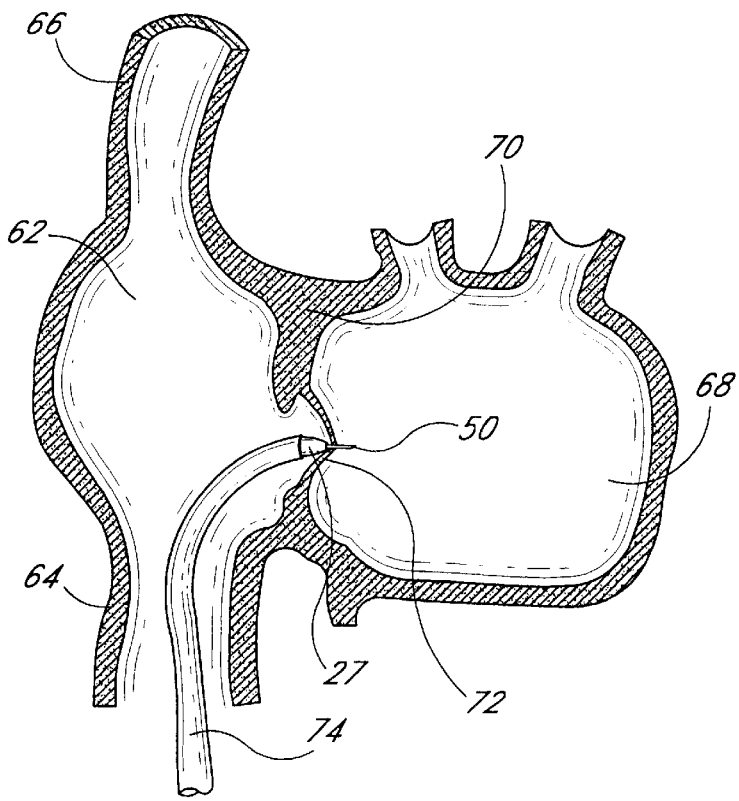
FIG. 8 is a cross-sectional view as in FIG. 4, showing tissue distention or "tenting" as the needle punctures the fossa ovalis.
Figure 9:
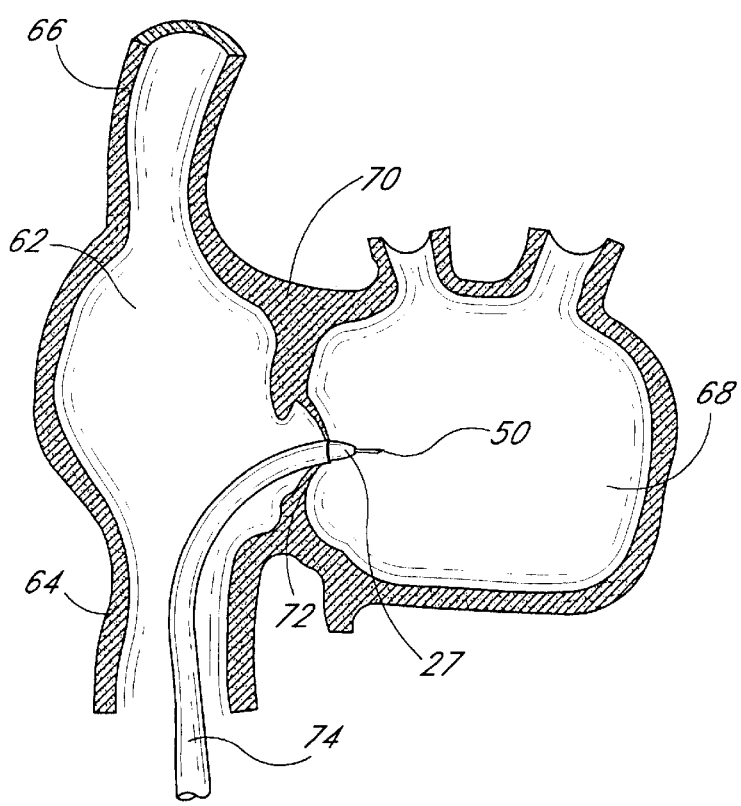
FIG. 9 is a cross-sectional view as in FIG. 8, showing tissue distention as the dilator is advanced through the fossa ovalis.
Figure 10:
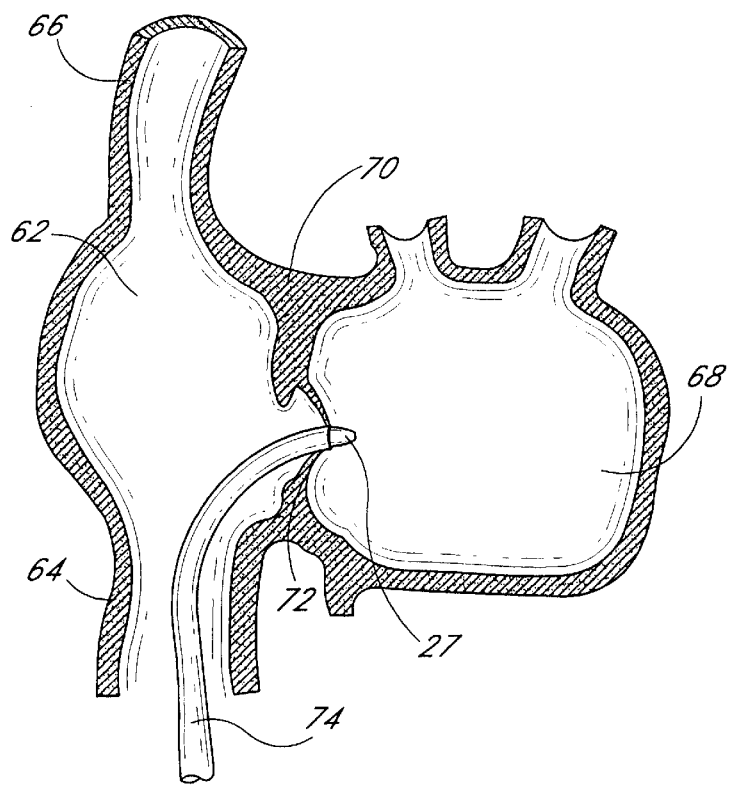
FIG. 10 is a cross-sectional view as in FIG. 9, illustrating the sheath, which has been advanced over the dilator and through the septum.

The guidewire 76 is thereafter distally advanced to access the superior vena cava 66. See FIG. 5. The dilator 20 and sheath 74 are thereafter advanced into the superior vena cava as illustrated schematically in FIG. 6. The guidewire 76 is proximally retracted.

When the sheath 74 and dilator 20 are in the superior vena cava and the guide wire has been removed, a transeptal needle 44 is advanced through the central lumen 39 of the dilator 20 and sheath 74 . The transeptal needle 44 is advanced (possibly with a stylet in place) to a point that the stylet tip is just inside the distal tip of the sheath 74 and dilator 20, a position previously noted by the operator, and the stylet is withdrawn from the transeptal needle.

The remaining combination of the sheath 74 with the dilator 20 having the transeptal needle therein, is then drawn proximally from the superior vena cava while the preset curve 25 at the distal region of dilator 20 causes the tip of the sheath-dilator-transeptal needle combination to "drag" along the wall of the right atrium and the septum 70. See FIG. 7. Depending upon the particular embodiment of the transeptal access system, some differences in the access method will occur at this point.

Figure 2:
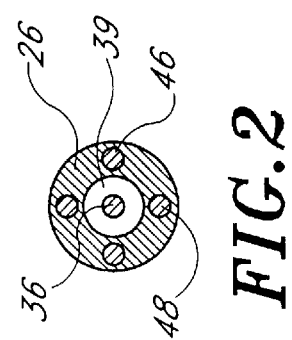
FIG. 2 is a cross-sectional view taken along the line 2—2 in FIG. 1.

For example, in the reflected light embodiment disclosed in connection with FIGS. 1–3, the light source and detector 37 will likely need to be calibrated once the dilator 20 has been placed inside the right atrium 62 but before the tip has been placed against the septum 70. The tip of the dilator 20 is then positioned against the septum 70 by distal advancement through the sheath 74. The tip is then dragged along the septum by proximal traction on the dilator 20 until the tip pops onto the fossa 72. Once the tip is positioned on the fossa 72, the characteristic color at the fossa is detected by the detector 37. A responsive audio or visual signal is generated, confirming that the catheter 20 is now properly positioned at the fossa ovalis 72.

The physician is normally assisted during placement, as in the entire procedure, by fluoroscopy or other visualization techniques. To assist in such visualization, the distal tip of sheath 74 and the distal tip of dilator 20 may be provided with a radiopaque marker. In addition, some physicians find it desirable to infuse a radiopaque dye through the transeptal needle at various stages of the procedure to assist in visualization, particularly following the transeptal puncture.

After the tip of the sheath-dilator-transeptal needle combination has been placed in the desired location against the fossa ovalis 72, the transeptal needle 44 is abruptly advanced to accomplish a quick puncture. See FIG. 8. Immediately after the puncture, one medical technique is to confirm the presence of the tip 50 of the transeptal needle 44 within the left atrium 68. Confirmation of such location of the tip 50 of the transeptal needle 44 may be accomplished by monitoring the pressure sensed through the transeptal needle lumen to ensure that the measured pressure is within the expected range and has a waveform configuration typical of left atrial pressure. Alternatively, proper position within the left atrium 68 may be confirmed by analysis of oxygen saturation level of the blood drawn through the transeptal needle 44; i.e., aspirating fully oxygenated blood. Finally, visualization through fluoroscopy alone, or in combination with the use of dye, may also serve to confirm the presence of the tip 50 of the transeptal needle 44 in the left atrium 68.

Figure 11:
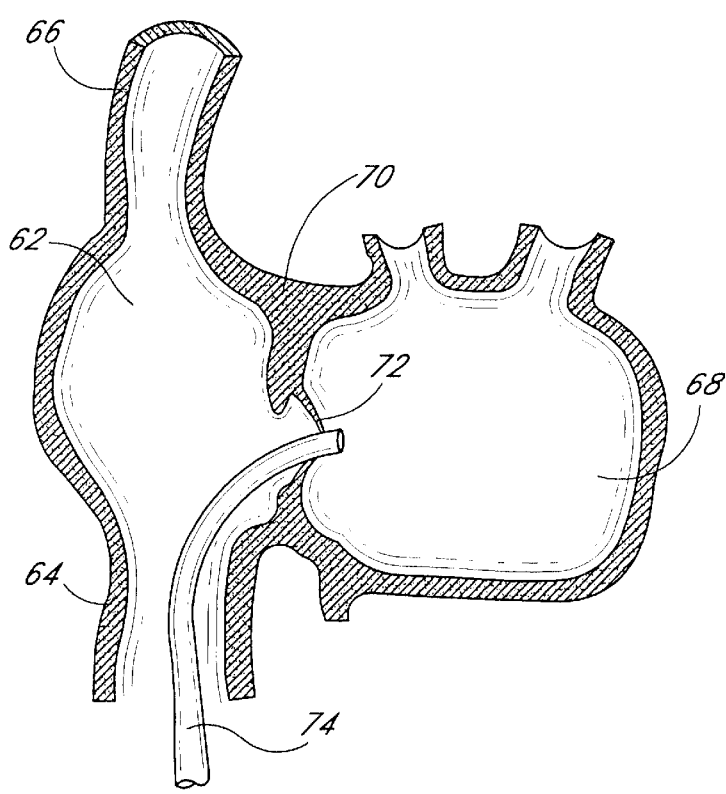
FIG. 11 is a cross-sectional view as in FIG. 10, with the dilator removed, leaving the sheath in place across the fossa ovalis.

After placing the transeptal needle tip 50 within the left atrium 68, the tip 27 of the dilator 20 is advanced through the septum 70 and into the left atrium 68. See FIG. 9. Typically, care is taken to ensure that, at the same time of advancing the dilator and sheath tip into the left atrium, the tip of the transeptal needle is not advanced a sufficient distance that the needle 44 can damage the opposing wall of the left atrium 68. When the tapered needle tip 27 of dilator 20 appears to have entered the left atrium 68, the transeptal needle 44 is withdrawn. The sheath 74 is then advanced into the left atrium 68, either by advancing the sheath 74 alone over the dilator 20 or by advancing the sheath 74 and dilator 20 in combination. See FIG. 10. The dilator 20 is then withdrawn from sheath 74 when the latter has been advanced into the left atrium, thus leaving the main lumen of sheath 74 as a clear pathway to advancing further diagnostic or therapeutic instruments into the left atrium. See FIG. 11.

Although the present invention has been described in terms of certain preferred embodiments, other embodiments will become apparent to those of skill in the art in view of the disclosure herein. Accordingly, the scope of the present invention is not intended to be limited by the specific embodiments disclosed herein, but, rather, by the full scope of the claims attached below.

What is claimed is:

1. A method of locating the fossa ovalis, comprising the steps of:

positioning the distal tip of a catheter in the heart, wherein the distal tip is in contact with the septum of the heart;

propagating a signal from the catheter;

receiving a return signal;

moving the tip to a position in which the return signal is indicative of the fossa ovalis; and penetrating the fossa ovalis with the catheter.

2. A method of locating the fossa ovalis as in claim 1, wherein the propagating a signal step comprises propagating an ultrasound signal.

3. A method of locating the fossa ovalis as in claim 1, wherein the propagating a signal step comprises propagating an electromagnetic signal.

4. A method of locating the fossa ovalis as in claim 3, wherein the electromagnetic signal is in the UV-visible range.

5. A method of locating the fossa ovalis as in claim 4, wherein the electromagnetic signal comprises multiple wavelengths.

6. A method of locating the fossa ovalis as in claim 1, wherein the position is in contact with the fossa ovalis.

7. A method of locating the fossa ovalis, comprising the steps of:

bringing a catheter into contact with the surface of the septum between the right and left atria;

moving the catheter along the septum; and monitoring for a color which indicates that the catheter has located the fossa ovalis.

8. A method of locating the fossa ovalis as in claim 7, wherein the monitoring step comprises detecting light.

9. A method of locating the fossa ovalis as in claim 8, wherein the monitoring step comprises detecting ultraviolet light.

10. A method of locating the fossa ovalis as in claim 8, wherein the monitoring step comprises detecting visible light.

11. A method of locating the fossa ovalis as in claim 10, wherein the light comprises at least one of red, green and blue light.

12. A method of locating the fossa ovalis as in claim 8, wherein the monitoring step comprises detecting infrared light.

13. A method of locating the fossa ovalis as in claim 8, wherein the monitoring step comprises detecting reflected light.

14. A method of locating the fossa ovalis as in claim 8, wherein the monitoring step comprises monitoring light propagated from a source in the left atrium.

15. A method of locating the fossa ovalis as in claim 7, further comprising the step of calibrating the catheter.

16. A method of locating the fossa ovalis as in claim 7, further comprising the steps of transmitting light distally through the catheter to the septum, and transmitting reflected light proximally through the catheter to a detector.

17. A method of locating the fossa ovalis as in claim 16, further comprising the step of generating an indicia in response to a change in reflected light at the fossa ovalis.

18. A method of locating the fossa ovalis as in claim 17, wherein the indicium comprises an audio or visual signal.

19. A method for locating the fossa ovalis, comprising the steps of:

positioning the distal tip of a catheter in the heart;

propagating a signal from the catheter;

receiving a return signal;

moving the tip to a position in which the return signal is indicative of the fossa ovalis; and penetrating the fossa ovalis with a needle provided at the distal tip of the catheter.

20. The method of claim 19, wherein the needle is axially moveable from the distal tip of the catheter.

21. A method for locating the fossa ovalis, comprising the steps of:

positioning the distal tip of a catheter in the heart, wherein the distal tip is in contact with the septum of the heart;

propagating a signal from the catheter;

receiving a return signal; and moving the tip to a position in which the return signal is indicative of the fossa ovalis.

22. A method of locating the fossa ovalis, comprising the steps of:

bringing a catheter into contact with the surface of the septum between the right and left atria;

moving the catheter along the septum;

monitoring for a color which indicates that the catheter has located the fossa ovalis; and penetrating the fossa ovalis with the catheter.

23. A method for accessing the left atrium of the heart, comprising:

delivering a signal transmitting and receiving device into the right atrium of the heart, the signal transmitting and receiving device when delivered being positioned adjacent the intraatrial septum between the right atrium and left atrium of the heart;

transmitting and receiving a signal from the signal transmitting and receiving device to determine the location of the fossa ovalis;

forming an opening in the fossa ovalis between the right atrium and the left atrium; and advancing an elongate hollow body through the opening in the fossa ovalis from the right atrium into the left atrium to provide access into the left atrium through the elongate hollow body.

24. The method of claim 23, wherein forming the opening in the fossa ovalis comprising piercing the fossa ovalis with a needle.

25. The method of claim 24, wherein the needle is provided at a distal end of the elongate hollow body.

26. The method of claim 25, further comprising withdrawing the needle from the elongate hollow body after the needle pierces the fossa ovalis and the elongate hollow body is advanced through the opening in the fossa ovalis.

27. The method of claim 23, wherein the elongate hollow body is a dilator.

28. The method of claim 27, further comprising advancing a sheath through the opening in the fossa ovalis from the right atrium into the left atrium, the sheath being provided over the dilator.

29. The method of claim 28, wherein the dilator and sheath are advanced through the opening in the fossa ovalis simultaneously.

30. The method of claim 28, wherein the sheath is advanced over the dilator through the opening in the fossa ovalis after the dilator is advanced into the left atrium.

31. The method of claim 28, further comprising withdrawing the dilator from the sheath after the sheath has been advanced into the left atrium.

32. The method of claim 23, wherein the signal transmitting and receiving device comprises a light source and detector provided adjacent a distal end of the elongate hollow body.

33. The method of claim 32, wherein the elongate hollow body is a dilator having a preset bend near its distal end, and wherein delivering a signal transmitting and receiving device into the right atrium of the heart comprises:

delivering the dilator into the right atrium over a guidewire;

delivering a sheath into the right atrium, wherein when delivered, the sheath is positioned over the dilator;

advancing the guidewire into the superior vena cava;

advancing the dilator and sheath over the guidewire until distal ends of the dilator and sheath are located in the superior vena cava;

withdrawing the guidewire from the dilator;

advancing a needle through the guidewire until the needle is positioned adjacent the distal end of the dilator; and drawing the dilator and sheath proximally from the superior vena cava, whereby the preset curve of the dilator causes the distal ends of the sheath and dilator to be positioned adjacent the intraatrial septum.

34. The method of claim 23, wherein the signal transmitting and receiving device comprises fiber optics.

35. The method of claim 23, wherein transmitting and receiving a signal from the signal transmitting and receiving device comprises detecting light reflected at a surface or within the fossa ovalis.

36. The method of claim 23, wherein transmitting and receiving a signal from the signal transmitting and receiving device comprises detecting light reflected through the fossa ovalis by blood in the left atrium.

37. The method of claim 23, wherein transmitting and receiving a signal from the signal transmitting and receiving device comprises detecting light generated in the left atrium.

* * * * *

UNITED STATES PATENT AND TRADEMARK OFFICE
CERTIFICATE OF CORRECTION

PATENT NO.    : 6,650,923 B1
DATED         : November 18, 2003
INVENTOR(S)   : Michael D. Lesh, Alex K. Khairkhahan and Erik J. van der Burg It is certified that error appears in the above-identified patent and that said Letters Patent is hereby corrected as shown below:

<u>Title page,</u>
Item [75], Inventors, please replace the Inventor's name "Alex K. Khairkahan" with
-- Alex K. Khairkhahan --.

Signed and Sealed this

Thirteenth Day of April, 2004

JON W. DUDAS
*Acting Director of the United States Patent and Trademark Office*